United States Patent
Luo et al.

(10) Patent No.: US 7,087,559 B2
(45) Date of Patent: Aug. 8, 2006

(54) NON-FOAMING CLEANING AND CONDITIONING HAIR CARE COMPOSITIONS

(75) Inventors: Xiaochun Luo, New City, NY (US);
Ginger King, Valley Cottage, NY (US);
Kenneth Buckridge, Mahwah, NJ (US)

(73) Assignee: Avon Products, Inc., New York, NY (US)

( * ) Notice: Subject to any disclaimer, the term of this patent is extended or adjusted under 35 U.S.C. 154(b) by 0 days.

(21) Appl. No.: 10/320,305

(22) Filed: Dec. 16, 2002

(65) Prior Publication Data

US 2004/0116311 A1 Jun. 17, 2004

(51) Int. Cl.
*C11D 1/66* (2006.01)
*C11D 1/38* (2006.01)
*C11D 3/37* (2006.01)
*A61K 8/00* (2006.01)

(52) U.S. Cl. ...... 510/119; 510/122; 510/127; 510/128; 510/158; 510/404; 510/475; 424/70.1; 424/70.19; 424/70.31

(58) Field of Classification Search ...... 510/119, 510/122, 127, 128, 158, 404, 475; 424/70.1, 424/70.19, 70.31
See application file for complete search history.

(56) References Cited

U.S. PATENT DOCUMENTS

| | | | |
|---|---|---|---|
| 4,954,335 A | 9/1990 | Janchipraponvej | 424/70 |
| 5,116,605 A * | 5/1992 | Alt | 514/78 |
| 5,696,069 A | 12/1997 | Ito et al. | 510/123 |
| 5,756,076 A | 5/1998 | Cervantes et al. | 424/70.1 |
| 6,001,339 A * | 12/1999 | Finel et al. | 424/70.12 |
| 6,017,860 A | 1/2000 | Sajic et al. | 510/124 |
| 6,066,673 A | 5/2000 | McIver et al. | 514/634 |
| 6,190,645 B1 | 2/2001 | SaNogueira et al. | 424/59 |
| 6,211,186 B1 | 4/2001 | McIver et al. | 514/256 |
| 6,218,346 B1 | 4/2001 | Sajic et al. | 510/124 |
| 6,239,088 B1 | 5/2001 | George et al. | 510/131 |
| 6,335,000 B1 * | 1/2002 | Pratley | 424/47 |
| 6,586,378 B1 * | 7/2003 | Chandra | 510/120 |
| 2001/0029242 A1 | 10/2001 | Chandra | 510/119 |

FOREIGN PATENT DOCUMENTS

| | | |
|---|---|---|
| EP | 0618792 | 4/1999 |
| WO | WO 93/10750 | 6/1993 |
| WO | WO 98/48768 | 11/1998 |
| WO | WO 98/50005 | 11/1998 |
| WO | WO 99/18919 A2 | 4/1999 |
| WO | WO 99/18919 A3 | 4/1999 |
| WO | WO 00/06116 | 2/2000 |
| WO | WO 00/33798 | 6/2000 |
| WO | WO 00/41528 | 7/2000 |
| WO | WO 00/56273 | 9/2000 |
| WO | WO 01/05363 | 1/2001 |

* cited by examiner

*Primary Examiner*—Brian P Mruk
(74) *Attorney, Agent, or Firm*—Ohlandt, Greeley, Ruggiero & Perle, L.L.P.

(57) ABSTRACT

There are disclosed non-foaming cleaning compositions, and non-foaming cleaning and conditioning compositions for the hair. The compositions have at least one non-ionic surfactant and, optionally, at least one conditioning ingredient. Preferably, the compositions have a cosmetically acceptable vehicle. There are also disclosed methods for cleaning hair, cleaning and conditioning hair, and protecting color-treated hair that include topically applying the compositions of the present invention.

19 Claims, 1 Drawing Sheet

NON-FOAMING CLEANING AND CONDITIONING HAIR CARE COMPOSITIONS

BACKGROUND OF THE INVENTION

1. Field of the Invention

The present invention relates to hair care compositions. More particularly, the present invention relates to non-foaming or substantially non-foaming compositions for cleaning and/or moisturizing the hair. Still more particularly, the present invention relates to non-foaming or substantially non-foaming compositions for gently cleaning and/or conditioning the hair.

2. Description of the Related Art

A large variety of shampoos and conditioners are presently on the market as hair care products. Traditionally, shampoos have anionic surfactants as the primary cleaning component. While anionic surfactants are effective in cleaning, they do not condition the hair. They also have a disadvantage in that they are known to be the primary contributor to color fading in dyed hair. Traditional hair conditioning products do not clean the hair or scalp. Consumers who desire a high degree of cleaning and a high degree of conditioning generally use a separate shampoo and conditioner, which is thus a two step process.

To provide effective cleaning of the hair with gentle non-foaming products, as well as to provide products that effectively clean and condition the hair in one step, have long presented challenges to the hair care industry. Recently, two-in-one conditioning shampoo products have been developed. These products allegedly provide both cleaning and conditioning in one step with a single composition. However, such products use anionic surfactants. Consequently, such products are harsh on color-treated hair, provide only marginal conditioning benefit to the hair, and foam. Foaming hair care products require greater rinsing time than products that do not foam.

In spite of the various personal care products on the market for the cleaning and/or conditioning of hair, there remains a need for non-foaming compositions that provide effective and gentle cleaning and conditioning and are easily washed-off.

There is also a consumer desire for conditioning products that do not impart to the hair a greasy and/or limp feel. A hair composition that imparts conditioning while leaving the hair feeling clean to the touch is particularly desired by consumers. Clearly, consumers desire, and would benefit from, a conditioning product that may be used alone between shampoos to condition without leaving a feeling of chemical residue on the hair, i.e., "build-up".

The present invention conditions hair as effectively as a conditioner, while cleaning the hair as effectively as a shampoo. The present invention also provides a single composition or product that provides cleaning and conditioning and does not foam. Thus, the present invention provides a desired time saving benefit.

SUMMARY OF THE INVENTION

It is an object of the present invention to provide compositions that effectively clean the hair, and are non-foaming or at least substantially non-foaming.

It is another object of the present invention to provide compositions that effectively clean and condition the hair without leaving the hair limp or feeling greasy (or having build-up).

It is still another object of the present invention to provide cleaning compositions for the hair that are gentle to color-treated or dyed hair.

It is yet another object of the present invention to provide such non-foaming or substantially non-foaming compositions that are easily rinsed off the hair and are more environmentally friendly than foam compositions.

It is a further object of the present invention to provide a method for cleaning and/or conditioning the hair using compositions of the present invention.

These and other objects and advantages of the present invention, and equivalents thereof, are achieved by hair cleaning compositions, hair cleaning and conditioning compositions, compositions that protect color-treated hair, and methods of applying such compositions in accordance with the present invention. The hair cleaning compositions of the present invention have at least one non-ionic surfactant in an effective amount to clean hair. The present compositions can optionally have other surfactants. The amount of the non-ionic surfactant is greater than the amount of the other surfactant. The present compositions can also have a hair conditioning ingredient.

Preferably, the present compositions are free or substantially free of anionic surfactant. Should the present compositions have one or more anionic surfactants, the present composition must have at least one non-ionic surfactant(s) present in an amount greater than the total amount of anionic surfactants.

DETAILED DESCRIPTION OF THE INVENTION

Figure 1:
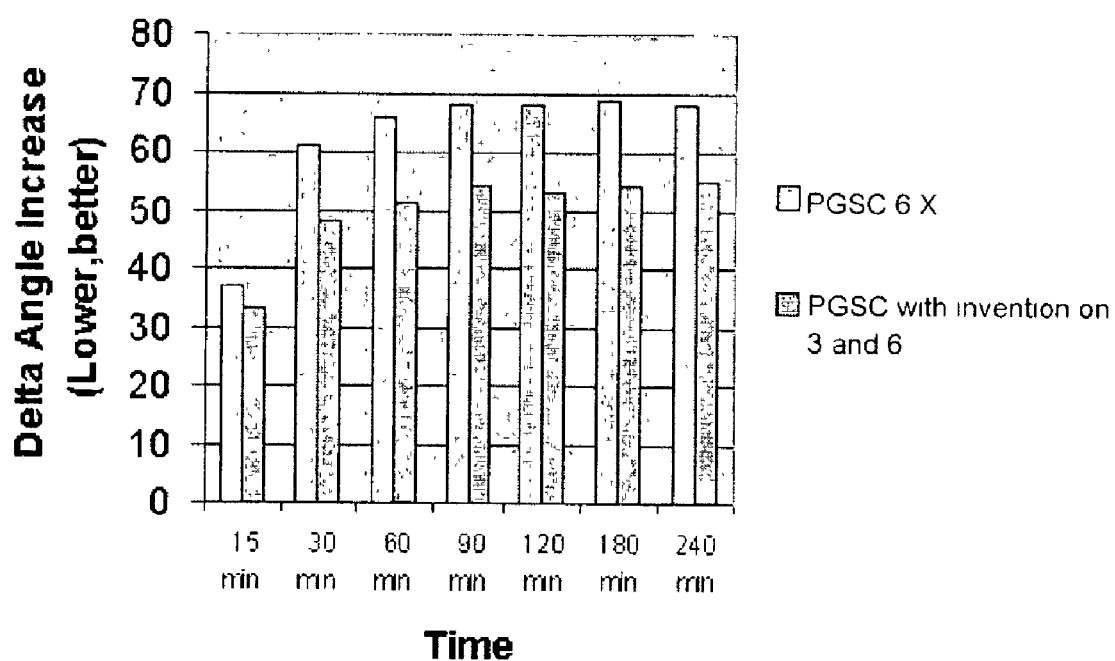
FIG. 1 is a graph showing Delta angle increase measured over time according to the present invention.

The compositions of the present invention have one or more active ingredients or blends of active ingredients that effectively clean and/or condition the hair in one step. The present compositions provide effective cleaning and conditioning to the hair and are notably gentle to color-treated hair. In addition, the compositions of the present invention may also be used to condition the hair between shampoos, with less build-up than prior art conditioning compositions. Further, the removal of build-up allows styling products to hold better.

To "effectively clean the hair" means to remove at least 20% sebum and/or residue from the hair. Effectively clean means to preferably remove at least 50% sebum and/or residue, and more preferably remove at least 90% of sebum and/or residue, from the hair. To "effectively condition the hair" means to provide smoothing of the hair cuticle. Smoothing of the hair cuticle also serves to decrease "tangling", which means proximate strands of hair becoming entwined.

The present invention also provides compositions that are entirely or substantially non-foaming. "Substantially non-foaming" means that compositions have little or no lather, suds, or foam when worked into the hair. The present compositions provide superior conditioning benefits in contrast to all known foaming or foam compositions. The present compositions are gentle, mild, and can also be rinsed from the hair faster than foaming compositions, thus providing a time-saving advantage.

The present compositions have one or more non-ionic surfactants. When used on the hair, the non-ionic surfactant cleans sebum and/or product residue. This cleaning benefit is provided substantially without foaming.

The non-ionic surfactant of the present invention includes, but is not limited to, at least one of the following: polysorbate 60 (Crillet 3), ppg-5-ceteth-20 (the polyoxypropylene, polyoxyethylene ether of cetyl alcohol), peg-20 sorbitan isostearate (Crillet 6), polysorbate 80 (Crillet 4), alkoxylated alcohols, alkoxylated polyol esters, or any combinations thereof. Especially preferred non-ionic surfactants are polysorbate 60 and ppg-5-ceteth-20.

The compositions of the present invention have at least one non-ionic surfactant in an amount effective to clean hair. The total hair cleaning effective amount of the one or more non-ionic surfactants in the present compositions is about 0.5 wt % to about 30 wt % based on the total weight of the composition. Preferably, the total amount of the non-ionic surfactant(s) is about 1 wt % to about 20 wt %, and more preferably about 3 wt % to about 12 wt %, based on the total weight of the composition.

The compositions of the present invention (especially when primarily a cleansing composition) can optionally have one or more other or optional surfactants. These optional surfactants can be any known surfactants. However, the total amount of the one or more non-ionic surfactants is greater than the total amount of all optional surfactants.

Preferably, the compositions of the present invention are free or substantially free of anionic surfactants. The term "substantially free" means that an anionic surfactant, if present, is in an amount less than 5 wt % based on the total weight of the composition. Thus, it is preferred that the optional surfactants are not anionic surfactants.

In the present compositions that have one or more anionic surfactants, the total amount of non-ionic surfactant on a weight basis is greater than the amount of the total amount of anionic surfactant. On a weight basis, the ratio of non-ionic surfactant(s) to anionic surfactant(s) is greater than about 1.5:1, preferably greater than about 5:1, more preferably greater than about 10:1, and optimally greater than about 100:1. Unlike the prior art that uses anionic surfactants as cleaning agents, the present compositions use one or more non-ionic surfactants as the primary cleaning ingredient.

In combination with the one or more non-ionic surfactants, the present compositions may conveniently employ any known active conditioning ingredient. The preferred active conditioning agent is also an optional or other surfactant. The most preferred optional surfactant/active conditioning agent is one or more cationic surfactants. A preferred cationic surfactant is palmitamidopropyltrimonium chloride.

Other active conditioning ingredients that can be used in the compositions of the present invention include, but are not limited to, one or more of the following: fatty alcohols (e.g., cetearyl alcohol), cationic polymers, conditioning polymers, cetyl esters, silicones or silicone compounds, silicone polymers, or any combinations thereof.

The silicone or silicone compounds useful as an active conditioning agent in the present compositions include, but are not limited to, one or more dimethicones, which are a mixture of fully methylated linear siloxane polymers end blocked with trimethysiloxy moieties.

In compositions of the present invention that have one or more active conditioning ingredients, the total amount of non-ionic surfactant(s) is preferably greater than the total amount of all active conditioning ingredient(s). The total amount of the active conditioning ingredients in the present compositions is a hair conditioning effective amount. A hair conditioning effective amount is preferably about 0.1 wt % to about 20 wt %, more preferably about 0.5 wt % to about 15 wt %, and most preferably about 2 wt % to about 10 wt %, based on the total weight of the composition.

On a weight basis, the ratio of non-ionic surfactant(s) to conditioning ingredient(s) is about 5:1 to about 6:5. Preferably, the ratio of non-ionic surfactant(s) to conditioning ingredient(s) is about 2:1 to about 4:3, and more preferably about 3:2.

The compositions of the present invention are topical compositions. Such topical compositions are preferably in the product form of a cream, but can be formulated in any suitable product form. Such other suitable product forms include, but are not limited to, a dispersion, an emulsion, a foundation, a gel, a liquid or a lotion. Preferably, the present compositions can be in the form of a homogeneous phase formulation or an emulsion. The emulsion form includes, but is not limited to, oil-in-water, water-in-oil, or multiple including triple, phase emulsions. These emulsions can cover a broad range of consistencies including thin lotions (which can also be suitable for spray or aerosol delivery), creamy lotions, light creams and heavy creams.

The present compositions preferably include a vehicle. A useful vehicle is one that is acceptable for topical applications. Useful vehicles include, but are not limited to, one or more aqueous systems, glycerins, $C_{1-4}$ alcohols, fatty alcohols, fatty ethers, fatty esters, polyols, glycols, water, or any combinations thereof.

Optionally, the present topical composition may include one or more adjuvants or adjuvant ingredients. Such adjuvants include, but are not limited to, one or more amphoteric surfactants (which can also be an optional surfactant), antioxidants, anti-dandruff agents, botanical extracts or ingredients, chelating agents, cooling agents (e.g., menthol), colorants, dyes, emollients, emulsifiers, fragrances, lubricants, moisturizers, pH adjusting agents, preservatives, proteins, protein hydrolysates or other protein derivatives, silicones, stabilizers, thickeners, viscosity modifiers, vitamins, UV agents, or any combinations thereof.

Such adjuvants are used in an amount up to about 20 wt % based on the total weight of the composition. Preferably, the adjuvants are present in an amount about 1 wt % to about 15 wt %, and more preferably about 5 wt % to about 10 wt %, based on the total weight of the composition.

The pH of the compositions of the present invention is about 3 to about 8.5. Preferably, the pH is about 4 to 7.5, and more preferably from about 4.5 to 7. The pH may conveniently be adjusted using pH adjusting agents such as citric acid, succinic acid, sodium hydroxide, triethanolamine, or any combinations thereof.

The compositions of the present invention can conveniently be used in effective amounts to clean the hair, to clean and condition the hair, and to protect color-treated hair in one step.

The present compositions may also be used between shampoos as a method of effectively conditioning the hair, with less build-up than conventional conditioning compositions. People with dry or damaged hair tend to overuse conditioning products because of a perceived need for them. However, when used together with styling products, the conditioners plasticize the styling products and make style retention less effective. Moreover, the conditioners also typically create residue build-up on the hair, which similarly affects the holding ability of the styling products, especially under high humidity. The removal of build-up allows styling products to hold better. The compositions of the present invention are gentle and mild enough to overcome the plasticization and build-up issues of the prior art, while providing effective conditioning. Preferably, a conditioning method of the present invention would include the steps of: applying the composition to and through the hair; leaving the composition on the hair for, preferably, greater than two minutes; and rinsing the hair.

The foregoing conditioning method may be augmented by adding one or more of the following steps:

(1) leaving the composition on the hair for greater than three minutes; or (2) applying heat, preferably by a warm towel, to the hair while the composition is on the hair.

Most preferably, the composition is left on the hair for about three to five minutes. Also most preferably, the heat is applied by wrapping the hair with a heated towel, which is preferably a moistened heated towel. Shampooing the hair beforehand is not necessary as the hair will be cleansed as it is conditioned. Simply rinsing the hair afterwards with water will suffice. Alternatively, the consumer may practice this method after or prior to shampooing. The conditioning method provided by the present invention is particularly useful for those consumers who have damaged hair, either from coloring, perming or other harsh treatments. The addition of cooling agents, such as menthol, is particularly pleasing/soothing to consumers when combined with the step of applying heat to the hair.

The following is an example of a preferred composition according to the present invention. Unless indicated otherwise, all amounts are in percentage by weight, based on the total weight of the composition.

EXAMPLE

| INGREDIENT | WT % |
| --- | --- |
| Non-Ionic Surfactant (e.g., polyoxyethylene (20M) sorbitan monostearate, PPG-5-Celeth-20) | 3 to 12 |
| Conditioning Agents (e.g., silicones such as dimethicone and/or dimethiconol, cationic polymers, such as guar HPT chloride, or cationic surfactants, such as palmitamidopropyltrimonium chloride, and/or fatty alcohols, such as cetyl alcohol or stearyl alcohol) | 2 to 10 |
| Adjuvants (e.g., menthol, sodium hyaluronate) | 0.5 to 5 |
| Preservatives (e.g., methylparaben, propylparaben) | 0.2 to 1 |
| Water | Qs to 100 |

A composition within the scope of the present invention as set forth above was compared against commercially available Pantene Smooth & Sleek Shampoo and Conditioner products. A bleached hair swatch was shampooed, conditioned and rinsed six consecutive times with the Pantene products. The swatch was then treated with a commercial mousse, and wrapped around a roller. The swatches were placed in an oven at 120 F for two hours for even distribution of heat. They were then removed and allowed to equilibrate at room temperature for thirty minutes. The roller was then removed to reveal a curled swatch. On a separate bleached swatch, the same regimen was followed, except, on the third and sixth time, the Pantene Conditioner was replaced with the conditioning composition of the present invention.

Both swatches were then measured using an industry Delta angle method. The Delta angle method measures the amount of curl retention loss over time. The lower the better. FIG. 1 shows the Delta angle increase measured over time as related to the comparison test procedures set forth above. As the data in FIG. 1 illustrates, the use of the composition of the present invention provides enhanced style hold ability, even up to four (4) hours.

It should be understood that the foregoing description is only illustrative of the present invention. Various alternatives and modifications can be devised by those skilled in the art without departing from the invention. Accordingly, the present invention is intended to encompass all such alternatives, modifications and variances that fall within the scope of the following claims.

What is claimed is:

1. A hair care cleaning and conditioning composition consisting essentially of:

at least one non-ionic surfactant present in a hair cleaning effective amount, and at least one hair conditioning ingredient present in an amount effective to condition hair, and further wherein said hair conditioning ingredient does not leave a feeling of build-up on the hair, wherein said composition is substantially non-foaming, wherein said at least one non-ionic surfactant is present in an amount of about 3 wt % to about 30 wt % based on the total weight of the composition, wherein the composition is substantially free of anionic surfactants, wherein said at least one non-ionic surfactant is present in an amount greater than said anionic surfactants, and wherein the ratio of said at least one non-ionic surfactant to said at least one hair conditioning ingredient on a weight basis is greater than about 1.2:1.

2. The composition of claim 1, further comprising at least one anionic surfactant.

3. The composition of claim 2, wherein the ratio of said at least one non-ionic surfactant to said at least one anionic surfactant on a weight basis is greater than 5:1.

4. The composition of claim 1, wherein said at least one non-ionic surfactant is selected from the group consisting of polysorbate 60, ppg-5-ceteth-20, peg-20 sorbitan isosterate, polysorbate 80, alkoxylated alcohols, alkoxylated polyol esters, and any combinations thereof.

5. The composition of claim 1, wherein said at least one non-ionic surfactant is selected from the group consisting of polysorbate 60, ppg-5-ceteth-20, and any combinations thereof.

6. The composition of claim 1, wherein said at least one non-ionic surfactant is present in an amount of about 3 wt % to about 20 wt % based on the total weight of the composition.

7. The composition of claim 1, wherein said at least one hair conditioning ingredient is selected from the group consisting of one or more fatty alcohols, cationic polymers, conditioning polymers, cationic surfactants, cetyl esters, silicones, silicone compounds, silicone polymers, and any combinations thereof.

8. The composition of claim 1, wherein said at least one hair conditioning ingredient is present in an amount of about 0.1 wt % to about 20 wt % based on the total weight of the composition.

9. The composition of claim 1, wherein said at least one hair conditioning ingredient is present in an amount of about 2 wt % to about 10 wt % based on the total weight of the composition.

10. The composition of claim 1, wherein the ratio of said at least one non-ionic surfactant to said at least one hair conditioning ingredient is about 5:1 to 1.2:1.

11. The composition of claim 10, wherein the ratio of said at least one non-ionic surfactant to said at least one hair conditioning ingredient is about 2:1 to about 4:3.

12. The composition of claim 1, further comprising a cosmetically acceptable vehicle.

13. The composition of claim 12, wherein the vehicle is selected from the group consisting of one or more aqueous systems, glycerins, $C_{1-4}$ alcohols, fatty alcohols, fatty ethers, fatty esters, polyols, glycols, water, and any combinations thereof.

14. The composition of claim 1, wherein the composition is in a product form selected from the group consisting of an aerosol spray, cream, emulsion, liquid, dispersion, gel, lotion, solution, and pump spray.

15. The composition of claim 14, wherein the product form is a cream.

16. A method of cleaning and conditioning hair comprising applying to the hair an effective amount of the composition of claim 1 for an effective period of time.

17. The method of claim 16, wherein the composition is left on the hair for two or more minutes.

18. The method of claim 17, wherein the composition is thereafter rinsed from the hair.

19. A method of cleaning and protecting color treated hair comprising applying to the hair the composition of claim 1.

* * * * *